United States Patent [19]

Pitman et al.

[11] 4,327,572

[45] May 4, 1982

[54] WEAR TESTER FOR SHOES

[75] Inventors: F. Judson Pitman, Portsmouth; Richard J. Chouinard, Barrington, both of N.H.

[73] Assignee: BRS, Inc., Beaverton, Oreg.

[21] Appl. No.: 159,298

[22] Filed: Jun. 13, 1980

[51] Int. Cl.³ .............................................. G01N 3/56
[52] U.S. Cl. ........................................................ 73/7
[58] Field of Search ............................................. 73/7

[56] References Cited

U.S. PATENT DOCUMENTS

| | | |
|---|---|---|
| 2,638,776 | 5/1953 | Aines . |
| 3,216,238 | 11/1965 | Bailey . |
| 3,427,859 | 2/1969 | Taub . |
| 3,516,281 | 6/1970 | Taub . |
| 3,608,372 | 9/1971 | Hovey et al. . |
| 4,096,733 | 6/1978 | Cohen . |
| 4,130,007 | 12/1978 | Hayashi . |

Primary Examiner—S. Clement Swisher

Attorney, Agent, or Firm—Schuyler, Banner, Birch, McKie & Beckett

[57] ABSTRACT

An apparatus for testing shoe durability by simulating the leg movements of a runner using a flexible artificial foot to repetitively drive the sole of a test shoe against an abrasive wear surface. The artificial foot is controlled by cam-operated plungers which reciprocate in synchronization causing the artificial foot to repetitively move through a leg cycle in which the heel is first driven against the wear surface followed by the ball and then the toe with empirically predetermined forces such that a normal wear pattern is produced. The wear surface is supported on a carriage which is longitudinally movable relative to the artificial foot in response to the forces of contact of the test shoe against the wear surface, the carriage including an adjustable spring for selecting a desired resistance to carriage movement. A mechanism is provided for tilting the wear surface to simulate running on an uneven surface.

19 Claims, 11 Drawing Figures

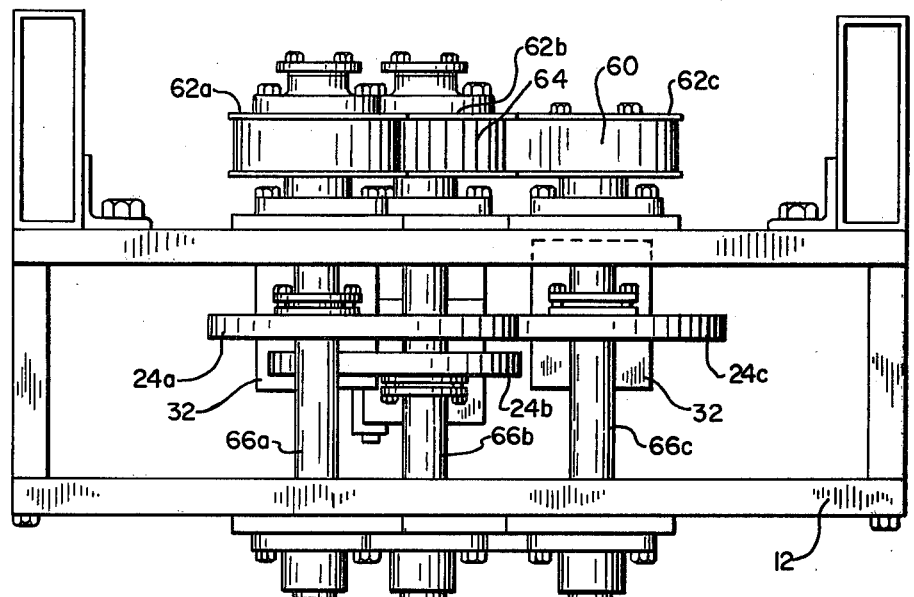
FIG. 3
FIG. 4
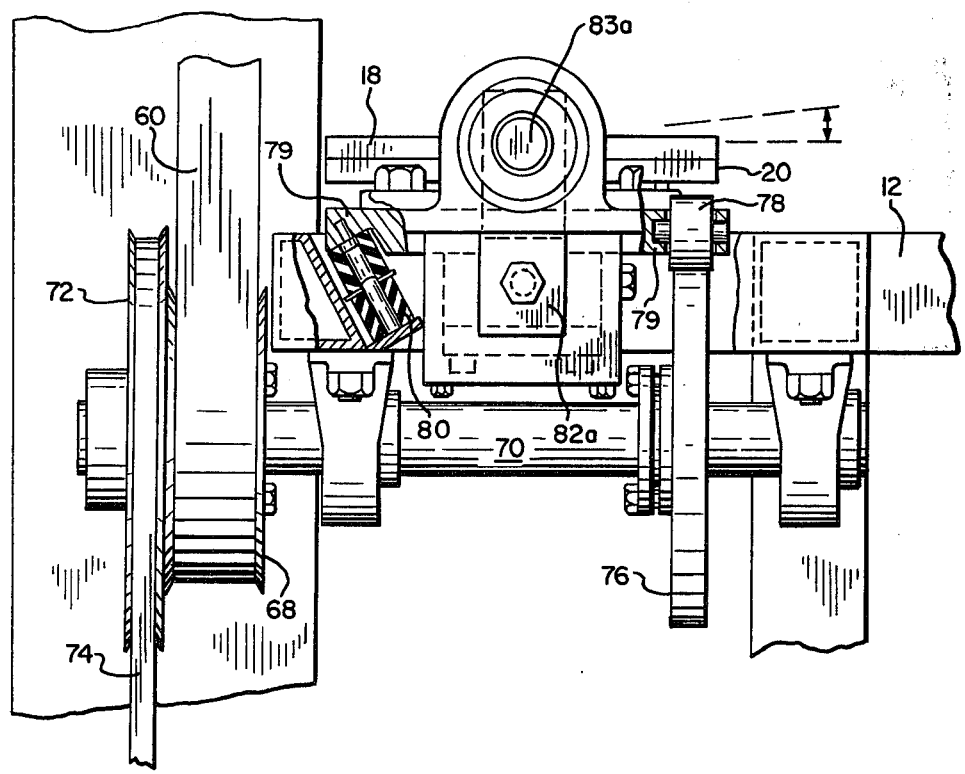

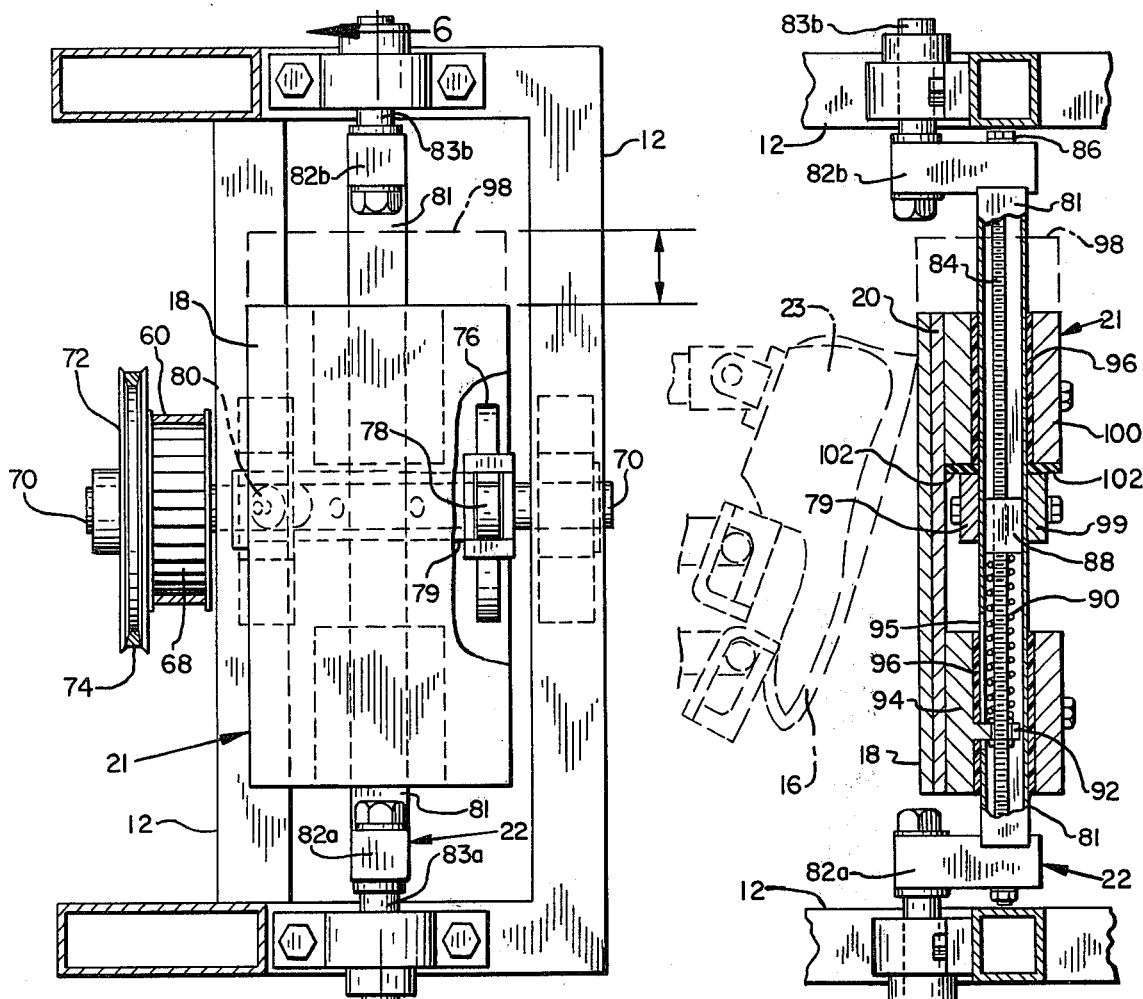
FIG. 5
FIG. 6
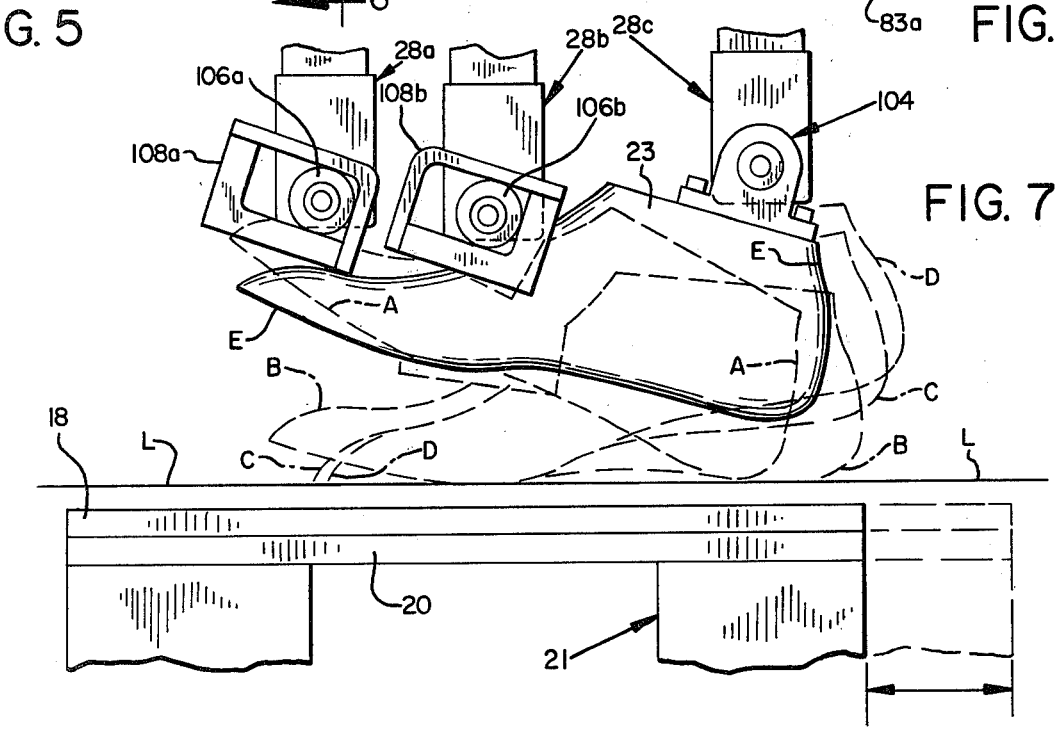
FIG. 7

WEAR TESTER FOR SHOES

BACKGROUND OF THE INVENTION

The present invention pertains to an apparatus for testing the durability of a sole of a shoe and has for its principal object the artificial simulation of actual outer sole wear on a test shoe.

It has been the practice in the prior art to test the durability of special purpose shoes, such as track shoes, football shoes, basketball shoes and the like, by subjecting test shoes to the rigors of actual sporting events using volunteer athletes. Such actual use testing is undesirable for a number of reasons. On the one hand, actual use testing is impractical in that it requires the production of a completely finished product, thereby precluding testing at an intermediate stage of development. From another standpoint, the time for obtaining test results is much too long. Furthermore, the parameters and environmental conditions of actual use testing are difficult to measure and control.

Accordingly, attempts have been made in the prior art to provide an apparatus for simulating actual outer sole wear. One such example is disclosed in U.S. Pat. No. 4,130,007. Although this patent discloses an apparatus which would appear to achieve the purpose of producing some measure of sole durability in a relatively short period of time, the apparatus is extremely intricate with a large number of moving parts which increases the likelihood of malfunction and resulting test interruption.

SUMMARY OF THE INVENTION

It is therefore a principal object of the present invention to provide a simplified shoe-testing apparatus for accurately predicting outsole durability in a relatively short period of time.

Another object of the present invention is the provision of a shoe-testing apparatus which enables the adjustment of the forces employed in driving a test shoe against a wear surface in order to empirically reproduce a normal wear pattern.

Another object of the present invention is the provision of a shoe-testing apparatus having a wear surface which is longitudinally movable in response to the force of contact of a test shoe, the resistance to movement of the wear surface being adjustable to permit empirical simulation of the shock-absorbing capability of the tissue and joints of the human body.

Other objects of the present invention are inherent in the novel features described in the following illustrative embodiment of the invention and recited in the appended claims.

BRIEF DESCRIPTION OF THE DRAWINGS

FIG. 3 is a top view of the apparatus of FIG. 1.

FIG. 4 is a side elevation view of a portion of the apparatus of FIG. 1 which simulates the ground surface to be engaged by a test shoe.

FIG. 5 is a top view of the portion of the apparatus that includes the ground simulation surface, the view being taken from line 5—5 of FIG. 1 looking in the direction of the arrows.

FIG. 6 is a cross section of a portion of the apparatus taken along line 6—6 of FIG. 5.

FIG. 7 is an enlarged view of the portion of the apparatus of FIG. 1 that includes an artificial foot, the foot being graphically illustrated in various operating positions in dotted outline.

DESCRIPTION OF THE PREFERRED EMBODIMENT

Figure 1:
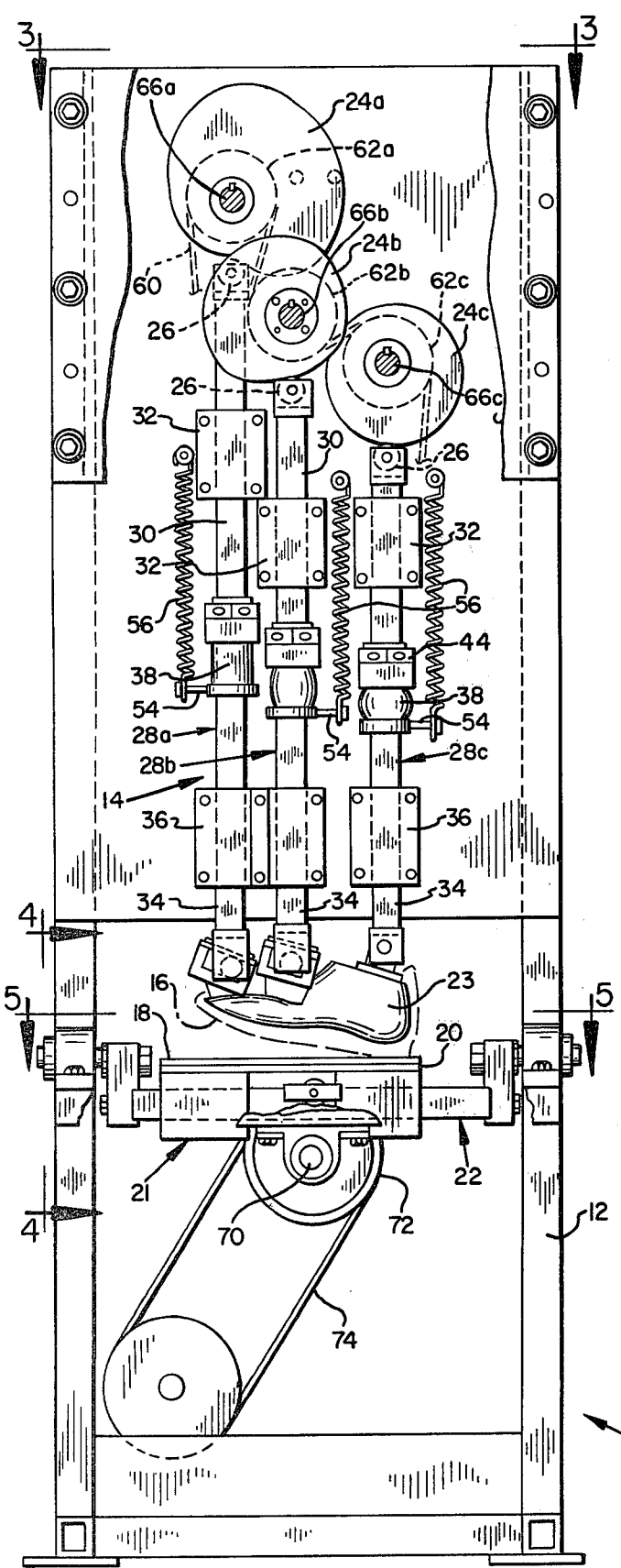
FIG. 1 is a front elevation of a wear tester apparatus in accordance with the present invention wherein portions of the frame have been removed to reveal the inner workings of the apparatus.

Referring to FIG. 1, a wear tester apparatus in accordance with the present invention is illustrated and designated generally by reference numeral 10. The wear tester 10 has an upstanding frame 12 within which a plunger assembly 14 is operable to repetitively drive a test shoe 16 (shown in phantom outline) against a ground simulation surface or wear surface 18 in order to simulate actual conditions of sole wear. The wear surface 18 is mounted on a strike plate 20 in a suitable manner (such as by unshown threaded fasteners) which readily allows replacement of the wear surface to maintain a desired abrasiveness. The strike plate 20 is supported from below by a carriage 21, which in turn is supported by a tilting mechanism 22 to be described more fully below. The test shoe 16 is secured on a somewhat flexible artificial foot 23 which is moved through a simulated leg cycle by the plunger assembly 14.

The plunger assembly 14 includes three rotating cams consisting of a toe cam 24a, a ball cam 24b and a heel cam 24c. The perimeter surfaces of the cams are engaged by respective cam followers which are identical and each labeled by reference numeral 26. The cyclical displacements of the cam followers 26 are conveyed to the artificial foot 23 by means of respective plunger mechanisms 28a, 28b and 28c which are pivotally attached to the foot 23 in a manner to be described more fully below in conjunction with FIG. 7.

Figure 2:
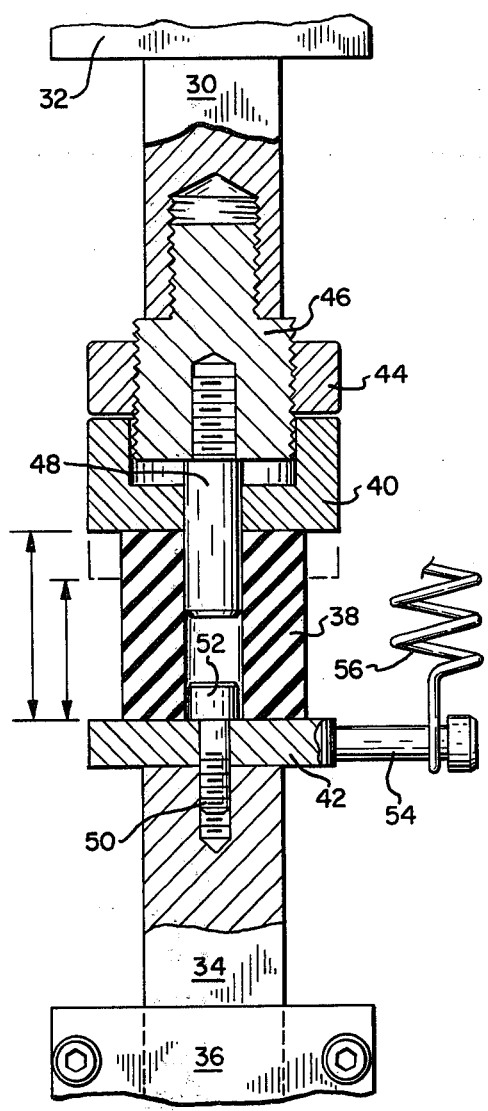
FIG. 2 is an enlarged view partially in cross section of a portion of the apparatus of FIG. 1.

Referring to the enlarged view of FIG. 2, the functionally equivalent elements of each plunger mechanism will be described. Each plunger mechanism has an upper rod 30 extending through an upper guide block 32 to the respective cam follower, and lower rod 34 extending through a lower guide block 36 to the respective attachment to the artificial foot. Disposed between the rods 30 and 34 is a force adjustment mechanism including an elastomeric cushion 38 which is compressed between a cup-shaped collar 40 and a disk 42 during the lower portion of the cam follower displacement cycle. Force adjustment is achieved by changing the overall length of the plunger mechanism. This is accomplished by varying the vertical position of a lock nut 44 with respect to a threaded connecting member 46 which is secured to the bottom of the upper rod 30. A locating pin 48, which is secured to the member 46, projects down through the collar 40 into a cylindrical aperture within the elastomeric cushion 38 thereby maintaining the cushion 38 in coaxial alignment with the rods 30 and 34. A bolt 50 secures the disk 42 to the top of the rod 34. The bolt 50 preferably has an elongated cylindrical head 52 which assists in maintaining proper alignment of the cushion 38. Another bolt 54 extends horizontally out from the disk 42 to provide an attachment for a return spring 56.

In order to synchronize the movements of the plunger assembly 14, the cams 24a, 24b and 24c are all driven by a single timing belt 60, as seen best in FIG. 3. The timing belt 60 is wound around three sprockets 62a, 62b and 62c, each having teeth, such as those labeled 64, for engaging mating teeth on the belt 60. The sprockets 62a, 62b, and 62c are secured for rotation with shafts 66a, 66b and 66c for driving the respective cams 24a, 24b and 24c.

Referring to FIGS. 4 and 5, the timing belt 60 extends down the back of the apparatus 10 and loops around a sprocket 68 which is secured to a shaft 70 located below the strike plate 20. The shaft 70 is rotated by means of a pulley 72 which in turn is rotated by means of a motor-driven belt 74. Secured to the shaft 70 is a cam 76 for intermittently lifting a cam follower 78 which is secured to one side of a rocker arm 79. Tilting of the rocker arm 79 causes the wear surface 18 to tilt through a slight angle as indicated by the double-pointed arrow in FIG. 4. A mechanism 80, which in this embodiment includes two axially aligned elastomeric rings mounted on the frame 12, acts against the other side of the rocker arm 79 to cause the wear surface 18 to resiliently return to a generally horizontal position. It will be appreciated that an alternative way of resiliently returning the wear surface 18 to its normal horizontal position can comprise a return spring (not shown) mounted adjacent to the cam follower 78 and adapted to pull that side of the rocker arm 79 down so that the cam follower 78 continuously engages the cam 76.

Referring now to FIG. 6, the details of the tilting mechanism 22 and related elements will be described. The tilting mechanism 22 includes a hollow yoke 81 supported at its opposite ends by pivot arms 82a and 82b which are secured to respective coaxial shafts 83a and 83b. The shafts 83a and 83b are pivotally supported by the frame 12 and define a tilt axis which longitudinally bisects the wear surface 18. Extending through the hollow interior of the yoke 81 is a threaded rod 84 having a hexagonal head 86 at one end. Disposed within the yoke 81 and threaded onto the rod 84 is a block 88 whose longitudinal position within the yoke 81 can be adjusted by turning the head 86 of the rod 84. The block 88 preferably has flat sides which slidably abut flat interior walls of the yoke 81 to prevent rotation of the block when the rod 84 is turned. A spring 90 is held under tension between the block 88 and a retaining bar 92 which extends down from a forward portion 94 of the carriage 21. The retaining bar 92 passes through a longitudinal slot 95 in an upper wall of the yoke 81 and extends down to surround the rod 84. The carriage 21 reciprocates along the yoke 81 in response to the simulated running action of the shoe 16 against the wear surface 18. Accordingly, the surfaces of the carriage 21 that make sliding contact with the yoke 81 are preferably coated with a material 96 which exhibits a low coefficient of friction. The carriage 21 is shown in its forwardmost position in FIGS. 5 and 6 and its rearwardmost position is indicated by the dashed outline labeled by the numeral 98. The range of movement of the wear surface 18 is therefore represented by the double-pointed arrow in FIG. 5. As seen best in FIG. 6, the rocker arm 79 is secured to the yoke 81 by means of a clamp plate 99 bolted to the rocker arm 79 on both sides of the yoke 81. The rocking motion of the rocker arm 79 is thereby transmitted through the yoke 81 to the carriage 21. Affixed to a forward face of a rearward portion 100 of the carriage 21 is an elastomeric bumper 102. When the return spring 90 brings the carriage 21 back to its forwardmost position, the bumper 102 will absorb the shock of impact against the rocker arm 79 and clamp plate 99. It will be appreciated that the slot 95 permits free longitudinal movement of the retaining bar 92 during reciprocation of the carriage 21 along the yoke 81.

Referring now to FIG. 7, the details of the attachments of the plunger assembly 14 to the artificial foot 23 will be described. The heel plunger mechanism 28c terminates in a pivotal attachment 104 above the heel of the artificial foot 23 in a manner which simulates the human ankle joint. The toe and ball plunger mechanisms 28a and 28b terminate in rollers 106a and 106b, respectively. The rollers are pivotally disposed in respective toe and ball attachments 108a and 108b secured to the artificial foot 23. The attachments 108a and 108b are slotted to permit longitudinal movement of the associated portions of the artificial foot relative to the rollers 106a and 106b, which are restricted to vertical translational movements with their respective plunger mechanisms 28a and 28b. Since the artificial foot 23 is allowed to pivot about the heel attachment 104, the toe and ball attachments 108a and 108b tend to move through arcs centered about the heel attachment 104 as the plunger mechanisms 28a, 28b and 28c move vertically.

Figure 8:
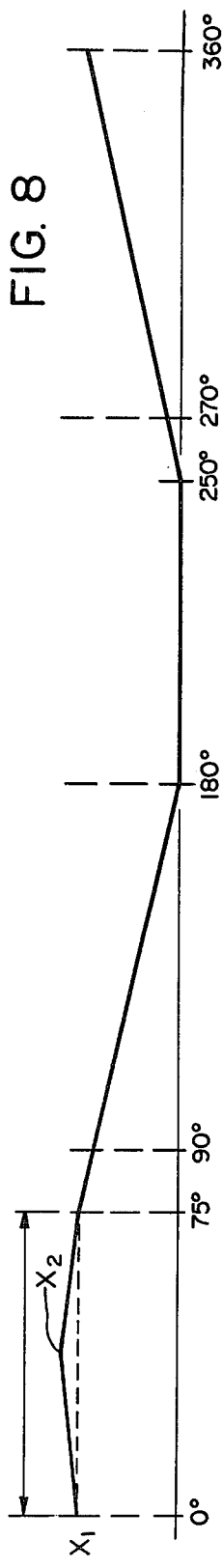
FIGS. 8-10 are displacement diagrams for the vertical movements of the heel, ball and toe portions, respectively, of the artificial foot.
Figure 9:
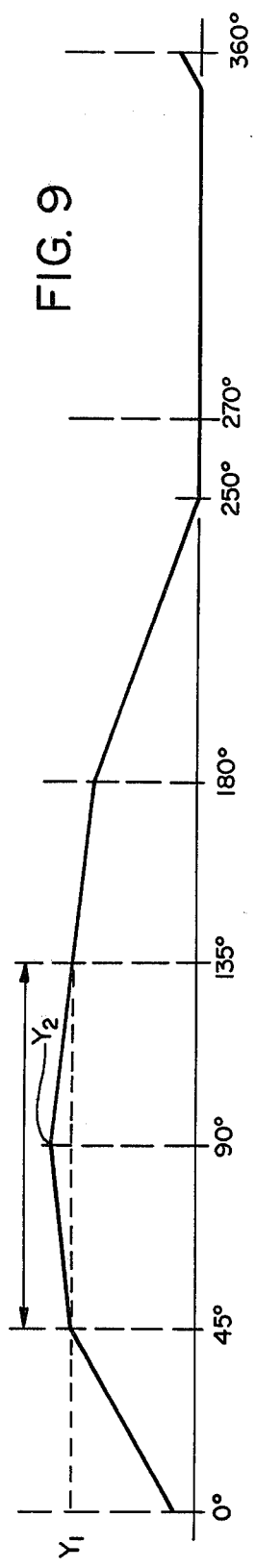
Figure 10:
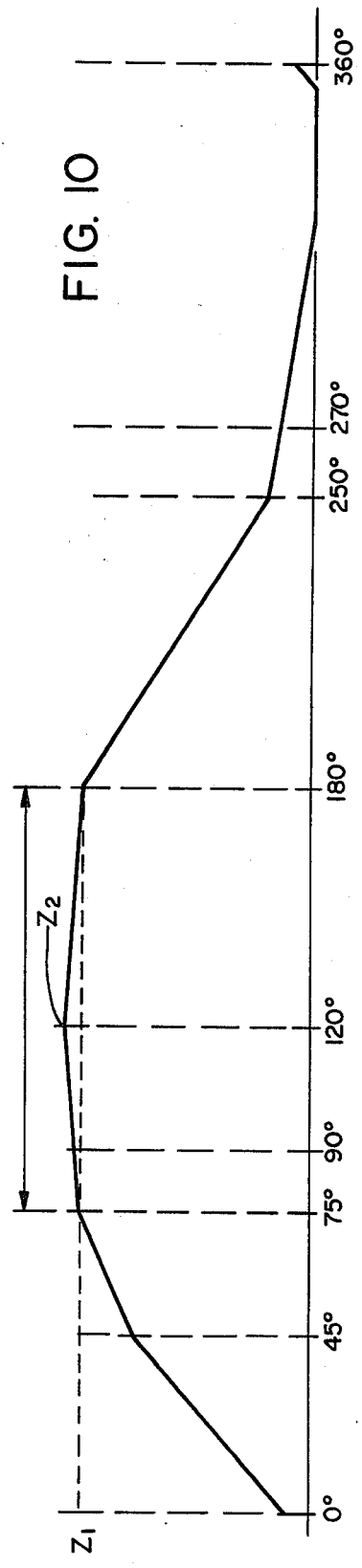

The simulated leg cycle can best be understood by reference to the displacement diagrams of FIGS. 8–10 in conjunction with the various positions of the artificial foot 23 illustrated in FIG. 7. The test shoe 16 depicted in FIGS. 1 and 6 has been left out of FIG. 7 for clarity of illustration of the various positions. When the artificial foot 23 comes down to the level of a reference line L, the test shoe would actually make contact with the wear surface 18. Accordingly, it will be understood that where the artificial foot 23 is shown meeting the reference line L, the corresponding portion of the sole of the test shoe would be in contact with the wear surface 18. The arbitrary starting point for purposes of the diagram of FIGS. 8–10 is indicated by the outline of the foot 23 labeled by reference letter A. With specific reference to FIG. 8, which is the heel displacement diagram, it will be appreciated that the heel of the test shoe makes initial contact with the wear surface 18 at 0° when the plunger mechanism 28a is at the displacement level $X_1$. This point in the simulated leg cycle will be referred to as the heel strike. The amount of travel of the cam follower 26 associated with the heel cam 24c beyond the initial contact level $X_1$ determines the amount of force that is applied in compressing the test shoe against the wear surface 18. In this particular example, the additional cam follower travel is from the $X_1$ level to a peak level of $X_2$ corresponding to the bottom of the cam follower stroke. Since there is a degree of adjustment in each of the three plunger mechanisms as previously described with reference to FIG. 2, it will be appreciated that the displacement diagrams shown in FIGS. 8–10 merely exemplify one possible leg cycle among various leg cycles capable of being performed by adjusting the overall lengths of the plunger mechanisms. The provision of such adjustment means enables the operator to empirically develop a normal-appearing wear pattern by adjusting the forces of contact of the toe, ball and heel portions of the test shoe with the wear surface 18 so that the wear pattern correlates to but not necessarily reproduces, actual outer sole wear.

In the particular leg cycle which is depicted by the displacement diagrams in FIGS. 8–10, the heel of the test shoe will remain in contact with the wear surface 18 from the time of the heel strike at 0° to about 75°. During this period, the contact point of the heel moves from left to right due to the downward movement of the plunger mechanisms 28a and 28b causing the foot 23 to pivot about the attachment 104. At about 75° in the leg cycle, the position of the artificial foot 23 is depicted by the dashed outline labeled B. During this 75° period of the leg cycle, the heel of the test shoe is forced down into compression with the wear surface 18. Since the human foot is known to absorb some of the shock of contact with the ground, it is preferred that the artificial foot 23 comprises a somewhat compressible material. Most preferably, the foot 23 is made of laminated polyurethane suitable for proper flex and shock absorption. Furthermore, in order to simulate the shock absorption capability of the human leg, the plunger mechanisms 28a, 28b and 28c employ the somewhat compressible, elastomeric cushions 38, seen in FIGS. 1 and 2. By adjusting the lengths of the plunger mechanisms 28a, 28b and 28c as described above with reference to FIG. 2, a degree of control over the force of contact of the three corresponding portions of the test shoe with the wear surface 18 can be provided in a range from zero to a preferred maximum of about 500 pounds.

With specific reference to FIG. 9, the displacement of the ball plunger mechanism 28b causes the ball of the test shoe to contact the wear surface 18 at about 45° in the leg cycle when the mechanism 28b is at the displacement level $Y_1$. This position is depicted by the dashed outline B in FIG. 7 wherein the ball and heel of the artificial foot 23 are shown at the reference level L but the toe still remains slightly above such level. The maximum cam follower displacement for the ball cam 24b occurs at 90° in the cycle as indicated by level $Y_2$.

With specific reference to FIG. 10, the displacement of the toe plunger mechanism 28a causes the toe of the test shoe to contact the surface 18 at about 75° in the leg cycle when the mechanism 28a is at the displacement level $Z_1$. The maximum cam follower displacement for the toe cam 24a occurs at 120° in the cycle as indicated by level $Z_2$.

It will be appreciated that it is not necessary to raise the artificial foot 23 to the same height that would normally occur in actual running in order to produce a normal wear pattern on the sole of the test shoe 16. It is presently preferred that following cam follower strokes be employed: the maximum heel displacement, $X_2$, equals 1.43 inches; the maximum ball displacement, $Y_2$, equals 1.83 inches; and the maximum toe displacement, $Z_2$, equals 3.09 inches.

By comparing FIGS. 8 and 10, it will be appreciated that the toe and heel of the test shoe are only momentarily both in contact with the wear surface 18 at about the 75° point in the leg cycle. From about 75° to about 135°, the ball and toe of the test shoe remain in contact with the surface 18 as represented by the position of the artificial foot 23 relative to the reference line L as depicted by the dashed outline C in FIG. 7. During the period between about 135° and about 180° only the toe of the test shoe remains in contact with the surface 18 as represented by the dashed outline labeled D in FIG. 7. During the period from 75° to 180° the pivotal movement of the artificial foot 23 continues to cause the wear surface 18 to be forced from left to right in the view of FIG. 7. During the half-cycle from 180° to 360°, the artificial foot 23 is lifted away from the wear surface 18 allowing the carriage 21 to return the wear surface 18 to its forwardmost position (to the left in FIG. 7) under the influence of the return spring 90. The maximum range of longitudinal movement of the wear surface 18, which ordinarily will include a portion of left to right displacement after the 180° point in the leg cycle due to the momentum of the carriage 21, is indicated by the double-pointed arrow in FIG. 7. The full range of carriage movement will vary somewhat depending upon the amount of tension that is applied to the spring 90 seen in FIG. 6. As the tension is increased on the spring 90, such range of carriage movement or displacement of the wear surface 18 will be reduced slightly because the shoe 16 will tend to slide to a greater extent along the surface 18, thereby causing an abrasive wearing action to occur on the sole of the shoe 16.

Figure 11:
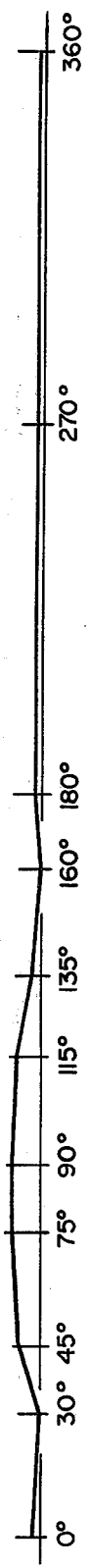
FIG. 11 is a displacement diagram of a cam follower which tilts the ground simulation surface.

Now referring to FIG. 11, in conjunction with FIG. 4, the displacement of the cam follower 78 will be described. From about 30° to about 75°, the cam follower 78 rises causing the wear surface 18 to tilt counterclockwise in the view of FIG. 4 to a maximum tilt angle where it remains until 90° in the leg cycle. From 90° to about 135°, the cam follower moves downwardly to bring the wear surface back toward a horizontal position. During the periods from 0° to 30° and from 135° to 180°, the wear surface is allowed to tilt slightly beyond horizontal in the other direction. During the period from 180° to 360°, the wear surface 18 is maintained in a generally horizontal position. The full range of displacement of the cam follower 78 is preferably 0.32 inch. The cam follower 78 in the present embodiment is located 3.0 inches horizontally to the right of the center of the shaft 83a in the view of FIG. 4. The actual range of tilt of the wear surface 18 is therefore only about 6° as indicated by the double-pointed arrow in FIG. 4.

From the foregoing description of the presently preferred embodiment of the invention, those skilled in the art will appreciate that the present invention accomplishes each of the aforementioned objects and that the presently preferred embodiment thereof, although described with extensive detail, can be modified in many respects without departing from the spirit and scope of the invention as defined in the appended claims.

What is claimed is:

1. An apparatus for testing the wear characteristics of the sole of a shoe, comprising:
   an upstanding frame;
   an abrasive wear surface supported by the frame;
   first means for carrying a test shoe with the sole thereof in operative proximity to the wear surface; and
   a plunger assembly supported by the frame and attached to the first means for repetitively driving the sole of the test shoe against the wear surface, the plunger assembly including a plurality of plunger mechanisms and means for reciprocating each plunger mechanism to cause the test shoe to move through a simulated leg cycle such that the sole of the test shoe repetitively strikes the wear surface.

2. The apparatus of claim 1 further comprising:
   a carriage for supporting the wear surface; and
   means for tilting the carriage during a period of the leg cycle when the sole of the test shoe makes contact with the wear surface.

3. The apparatus of claim 2 further comprising:
means for supporting the carriage to permit longitudinal movement of the carriage in response to the force of contact of the test shoe against the wear surface; and
means for resiliently returning the carriage to a starting position before the beginning of each new leg cycle.

4. The apparatus of claim 1 further comprising means for varying the length of each plunger mechanism to adjust the force of contact of the associated portions of the sole of the test shoe against the wear surface.

5. The apparatus of claim 1 further comprising a strike plate supported by the carriage, the strike plate having a surface upon which the wear surface is detachably secured to permit replacement of the wear surface.

6. An apparatus for testing the wear characteristics of the sole of a shoe, comprising:
an upstanding frame;
an abrasive wear surface supported by the frame;
an artificial foot for carrying a test shoe with the sole thereof in operative proximity to the wear surface;
a plurality of reciprocating plunger mechanisms supported by the frame for moving the artificial foot through a simulated leg cycle wherein the sole of the test shoe is repetitively driven against the wear surface; and
camming means for reciprocating each plunger mechanism.

7. The apparatus of claim 6 wherein the plunger mechanisms are three in number, each having attachments to the artificial foot for permitting the artificial foot to pivot about a point that simulates the human ankle joint.

8. The apparatus of claim 7 wherein the camming means includes toe, ball and heel cams for reciprocating respective plunger mechanisms so that the heel makes contact with the wear surface at a first time in the leg cycle and the ball and toe make contact with the wear surface at subsequent times in the leg cycle.

9. The apparatus of claim 8 further comprising:
a cam follower disposed on the end of each plunger mechanism remote from the pivotal attachments to the artificial foot;
means for resiliently urging each plunger mechanism toward the respective cam to hold each cam follower in continuous engagement against the respective cam; and
means for synchronously rotating the cams so that, in each leg cycle, the heel of the test shoe is lifted from the wear surface at a time when the ball is in contact with the wear surface and the ball and toe are lifted from the wear surface during successive subsequent times in the leg cycle.

10. The apparatus of claim 9 further comprising means for permitting the wear surface to move longitudinally with respect to the artificial foot in response to the pivotal movements of the artificial foot while portions of the test shoe are in contact with the wear surface.

11. The apparatus of claim 10 further comprising means for varying the resistance to longitudinal movement of the wear surface.

12. The apparatus of claim 10 further comprising means for tilting the wear surface while portions of the test shoe are in contact therewith.

13. The apparatus of claim 6 further comprising means associated with each plunger mechanism for adjusting the length of each plunger mechanism to adjust the forces of contact of the heel, ball and toe of the test shoe against the wear surface.

14. In an apparatus for testing the wear characteristics of a shoe, the method comprising:
carrying a test shoe having a sole to be tested on a movable support member;
moving said support member to drive the heel of the sole of the test shoe against an abrasive wear surface;
moving said support member to drive the ball of the sole of the test shoe against the wear surface while the heel remains in contact with the wear surface;
moving said support member to drive the toe of the sole of the test shoe against the wear surface while the ball remains in contact with the wear surface and substantially contemporaneously lifting the heel away from the wear surface;
subsequently moving said support member to lift the ball away from the wear surface;
subsequently moving said support member to lift the toe away from the wear surface; and
pivoting said support member in the area of the heel of the sole about a pivot point movable along substantially a single stationary vertical line during all phases of motion of said support member.

15. The method of claim 14 further comprising:
allowing the wear surface to move longitudinally rearward in response to the forces of contact of the test shoe with a predetermined resistance to longitudinal movement.

16. The method of claim 14 comprising:
transversely tilting the wear surface through a slight angle while portions of the test shoe are in contact with the wear surface.

17. In an apparatus for testing the wear characteristics of a shoe, the method comprising:
driving the heel of the sole of a test shoe against an abrasive wear surface;
driving the ball of the sole of the test shoe against the wear surface while the heel remains in contact with the wear surface;
driving the toe of the sole of the test shoe against the wear surface while the ball remains in contact with the wear surface and substantially contemporaneously lifting the heel away from the wear surface;
subsequently lifting the ball away from the wear surface;
subsequently lifting the toe away from the wear surface; and
transversely tilting the wear surface through a slight angle while portions of the test shoe are in contact with the wear surface.

18. An apparatus for testing the wear characteristics of the sole of a shoe, comprising:
a frame;
an abrasive wear surface supported by the frame;
an artificial foot for carrying a test shoe with the sole thereof in operative proximity to the wear surface;
first, second and third plunger assemblies supported by said frame, and first plunger assembly having a first rod supported for reciprocal motion in a first generally vertical plane, said second plunger assembly having a second rod supported for reciprocal motion in a second generally vertical plane, and said third plunger assembly having a third rod supported for reciprocal motion in a third generally vertical plane;

means for pivotably coupling a lower end of said first rod to said artificial foot at a fixed location in the area of the heel of the artificial foot;

means for pivotably coupling a lower end of said second rod to said artificial foot at a longitudinally movable point in the area of the ball of the artificial foot;

means for pivotably coupling a lower end of said third rod to said artificial foot at a longitudinally movable point in the area of the toe of the artificial foot; and means for sequentially reciprocating said first, second and third rods to move said artificial foot through a simulated leg cycle wherein the sole of the test shoe is repetitively driven against said wear surface.

19. An apparatus for testing the wear characteristics of the sole of a shoe, comprising:

a frame;

an artificial foot for carrying a test shoe having a sole to be tested;

an abrasive wear surface;

means for supporting said wear surface on said frame for reciprocating motion in a direction generally parallel to the lengthwise dimension of said artificial foot;

means for biasing said wear surface along its direction of reciprocating motion in a direction toward the toe portion of said artificial foot;

first, second and third plunger assemblies supported by said frame, said first plunger assembly having a first rod supported for reciprocal motion in a first generally vertical plane, said second plunger assembly having a second rod supported for reciprocal motion in a second generally vertical plane, and said third plunger assembly having a third rod supported for reciprocal motion in a third generally vertical plane;

means for pivotably coupling a lower end of said first rod to said artificial foot at a fixed location in the area of the heel of the artificial foot;

means for pivotably coupling a lower end of said second rod to said artificial foot at a longitudinally movable point in the area of the ball of the artificial foot;

means for pivotably coupling a lower end of said third rod to said artificial foot at a longitudinally movable point in the area of the toe of the artificial foot;

a first rotary driven cam supported by said frame adjacent said first rod and means for biasing said first rod into contact with said first cam;

a second rotary drive cam supported by said frame adjacent said second rod and means for biasing said second rod into contact with said second cam;

a third rotary driven cam supported by said frame adjacent said third rod and means for biasing said third rod into contact with said third cam;

means for rotating said first, second and third cams to move said first, second and third rods whereby said artificial foot moves through a simulated leg cycle to drive the sole of the test shoe repetitively against said wear surface; and means for tilting said wear surface while portions of the sole of the test shoe are in contact with it.

* * * * *